United States Patent [19]
Teves

[11] Patent Number: 5,315,991
[45] Date of Patent: * May 31, 1994

[54] CONNECTOR FOR ENDOTRACHEAL USES

[75] Inventor: Leonides Y. Teves, Bradenton, Fla.

[73] Assignee: Advanced Medical Concepts, Inc., Bradenton, Fla.

[*] Notice: The portion of the term of this patent subsequent to May 10, 2111 has been disclaimed.

[21] Appl. No.: 938,087

[22] Filed: Aug. 31, 1992

Related U.S. Application Data

[63] Continuation-in-part of Ser. No. 896,257, Jun. 10, 1992.

[51] Int. Cl.$^5$ .............................................. A61M 16/00
[52] U.S. Cl. ................................ 128/207.14; 128/912; 128/DIG. 26
[58] Field of Search ..................., 128/200.24, 202.27, 128/912, DIG. 26, 207.14, 207.15, 200.26

[56] References Cited

U.S. PATENT DOCUMENTS 4,674,496 6/1987 Svadjian et al. ..................... 128/912

*Primary Examiner*—Edgar S. Burr
*Assistant Examiner*—Aaron J. Lewis
*Attorney, Agent, or Firm*—Joseph C. Mason, Jr.; Ronald E. Smith

[57] ABSTRACT

A connector for joining an endotracheal tube and an integrally formed auxiliary lumen to a source of anesthesia and a preselected item of auxiliary equipment, respectively, includes a first pair of tubular mounting members on a proximal end of the connector that are closely radially spaced with respect to one another and longitudinally spaced from a second pair of tubular mounting members on a distal end of the connector that are closely radially spaced with respect to one another. A pair of parallel bores are formed in the base of the connector to provide fluid communication between associated, longitudinally spaced apart mounting members. The radially spaced mounting members on the proximal end slide-fittingly receive the respective distal ends of an anesthesia supply tube elbow connector and an auxiliary monitoring equipment tube, and the radially spaced mounting members on the distal end slide-fittingly receive the respective proximal ends of an endotracheal tube and an auxiliary lumen that is formed integrally with the endotracheal tube. A $CO_2$ port is formed in a tubular mounting member on the proximal end of the connector.

5 Claims, 2 Drawing Sheets

CONNECTOR FOR ENDOTRACHEAL USES

This is a continuation of copending application(s) Ser. No. 07/896,257, filed on Jun. 10, 1992, pending.

BACKGROUND OF THE INVENTION

1. Field of the Invention

This invention relates, generally, to endotracheal tubes of the type having an auxiliary lumen. More particularly, it relates to a connector therefor.

2. Description of the Prior Art

U.S. Pat. No. 4,967,759 to the present inventor discloses an endotracheal tube having an auxiliary lumen integrally formed therewith along the extent thereof.

Due to the close spacing of the auxiliary lumen and the main endotracheal tube, connection of the auxiliary lumen to preselected auxiliary equipment and connection of the main endotracheal tube to a supply source for the gaseous fluids to be administered to the patient is problematic. Note that a total of four primary items must be interconnected, i.e., the auxiliary equipment must be connected to the auxiliary lumen, and the supply source of the gas must be connected to the main endotracheal tube. The connector currently in use is designed to interconnect the proximal end of the main endotracheal tube and the distal end of a tube from said anesthesia supply source; no means are provided for interconnecting the auxiliary equipment and the auxiliary lumen. Thus, the proximal end of the auxiliary lumen merely abuts the connector when the proximal end of the endotracheal tube is connected to said connector. This results in a very unsatisfactory interconnection of the auxiliary equipment and the auxiliary lumen; the connector at the distal end of the tubing extending from the auxiliary equipment is brought around the endotracheal tube connector and brought into connection with the proximal end of the auxiliary lumen. An unacceptably sharp bend must be formed where the tubing from the auxiliary equipment meets the proximal end of the auxiliary lumen, resulting in an unacceptable constriction. Moreover, this arrangement requires the use of two separate connectors, i.e., a first connector for interconnecting the supply source and primary endotracheal tube and a second connector for interconnecting the auxiliary equipment and the auxiliary lumen. Since connectors are bulky, each connector interferes with the other when the various tubes are interconnected.

In the above-mentioned patent, this problem was overcome by making the auxiliary lumen substantially shorter than the main endotracheal tube so that the bend could be more gradual, thereby eliminating the constriction. However, this was unsatisfactory for other reasons. Specifically, the main endotracheal tube and auxiliary lumen are best constructed as a single unit. Thus, the manufacturing process is simpler and thus more cost effective if the main endotracheal tube and the auxiliary tube have a common length. Truncating the auxiliary lumen so that its proximal end is remote from the main connector thus drives up the manufacturing costs associated with the patented item. Moreover, shortening of the lumen still requires use of two connectors.

Still another shortcoming of the prior art is that the overall length of the connectors, when assembled, is too long. More particularly, a sleeve of elongate construction is used to interconnect the connector and an elbow member that engages a hose that extends from the source of anesthetizing gas. Thus, there are a total of three parts that must be assembled just to deliver the gas to the patient. Since all three parts are simply slide fit onto one another, it is incumbent upon the physician to hold the assembly together during the operation. The assemblies heretofore known are about eight centimeters in length; thus they are somewhat bulky and clumsy to deal with. Moreover, the physician must hold the assembly together by stretching his or her thumb upwardly so that it can overlie the elbow joint and thus hold the parts together.

What is needed, then, is a way to interconnect the lumen and the main tube to their respective pieces of equipment with a single connector and in the absence of sharp bends or truncated lumens. Moreover, an assembly of parts that would have less longitudinal extent than the assemblies now in use would be beneficial, because a shorter assembly of parts would be less bulky and would enable the anesthesiologist to hold the assembly together with less thumb reaching. However, at the time the present invention was made, the prior art, when considered as a whole as required by law, neither taught nor suggested to those of ordinary skill in this field how the extant problems could be resolved.

SUMMARY OF THE INVENTION

An improved connector includes an auxiliary pair of fittings on its proximal and distal faces, in addition to the conventional fittings for connection of the main endotracheal tube and the supply of anesthesia, so that the main endoctracheal tube and the auxiliary lumen may be manufactured as a single unit with the length of the auxiliary lumen being coextensive with the length of the main endotracheal tube. The auxiliary fitting on the proximal face of the novel connector receives the distal end of the auxiliary line from the auxiliary equipment, and the auxiliary fitting on the distal face of the connector provides a mount for the proximal end of the auxiliary lumen. This arrangement of parts also eliminates any bends in the line from the auxiliary equipment and in the auxiliary lumen.

Moreover, the sleeve for interconnecting the elbow of the prior art and the connector is eliminated so that the overall longitudinal extent of the novel assembly is substantially reduced.

Still another improvement is provided by eliminating the $CO_2$ port in the elbow and forming it in the novel connector instead. This lowers the cost of the elbow and adds no appreciable cost to the novel connector.

It is therefore understood that the primary object of this invention is to advance the art of endotracheal tubes in general.

Another broad object is to advance the art of connectors in general.

A more specific object is to provide an improved connector that combines connection means for four separate items in a single unit.

Another object is to provide a connector assembly of reduced longitudinal extent as compared to the assemblies heretofore known.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

Similar reference numerals refer to similar parts throughout the several views of the drawings.

DETAILED DESCRIPTION OF THE PREFERRED EMBODIMENT

Figure 1:
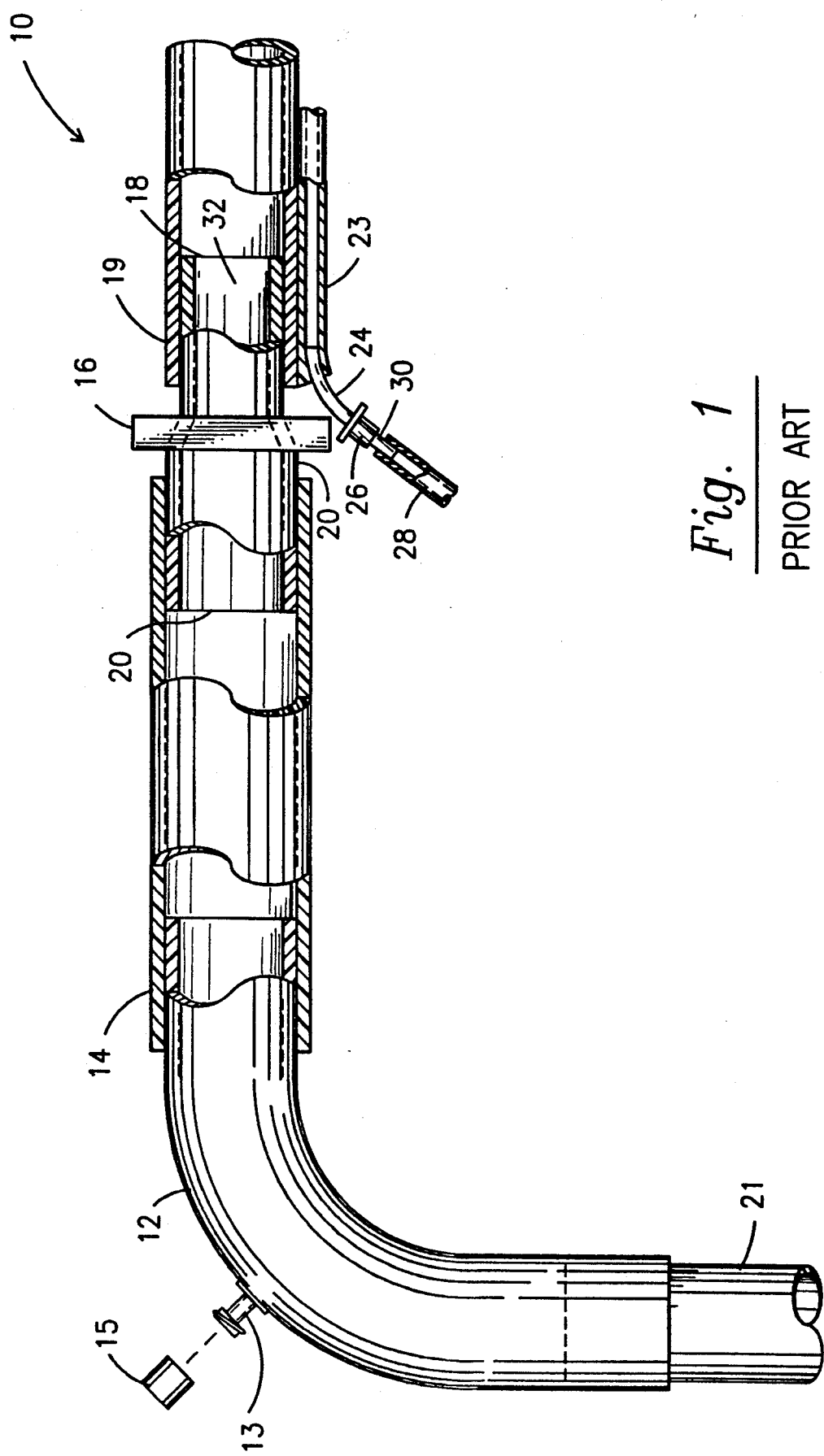
FIG. 1 is a side sectional view of a prior art connector.

FIG. 1 depicts a prior art assembly; it is denoted 10 as a whole. Assembly 10 includes elbow 12, sleeve 14, and main connector 16 that includes distal tubular projection or mounting member 18 onto which the proximal end of the main endotracheal tube 19 is slide-fittingly press fit. Said assembly further includes proximal tubular projection or mounting member 20 onto which the distal end of sleeve 14 is slide-fittingly press fit. Main supply tube 21 delivers the anesthesia from a source thereof to the proximal end of elbow 12, and main endotracheal tube 19 delivers said anesthesia to the patient's lungs.

Auxiliary lumen 23 is formed integral with main tube 19 as described in the present inventor's earlier patent as above-mentioned. Its proximal end tightly slide-fittingly receives distal tubular projection 24 of connector 26. Note that the proximal end of auxiliary lumen 23 is slightly distorted by said projection 24 due to the interference between connectors 16 and 26; note also the bend formed in tubular projection 24 due to the close proximity of connectors 16 and 26. The distal end of an auxiliary tube 28 slide-fittingly engages proximal tubular projection 30 of connector 26; tube 28 extends to pressure-sensing means, temperature sensing means, acoustical means, or other monitoring devices, none of which is shown, as explained in said patent.

Note at the left side of FIG. 1 that $CO_2$ port 13 is formed in elbow 12; cap 15 screw-threadedly engages said port 13. In the preferred embodiment of this invention, the diameter of part 13 is at least one millimeter.

Figure 2:
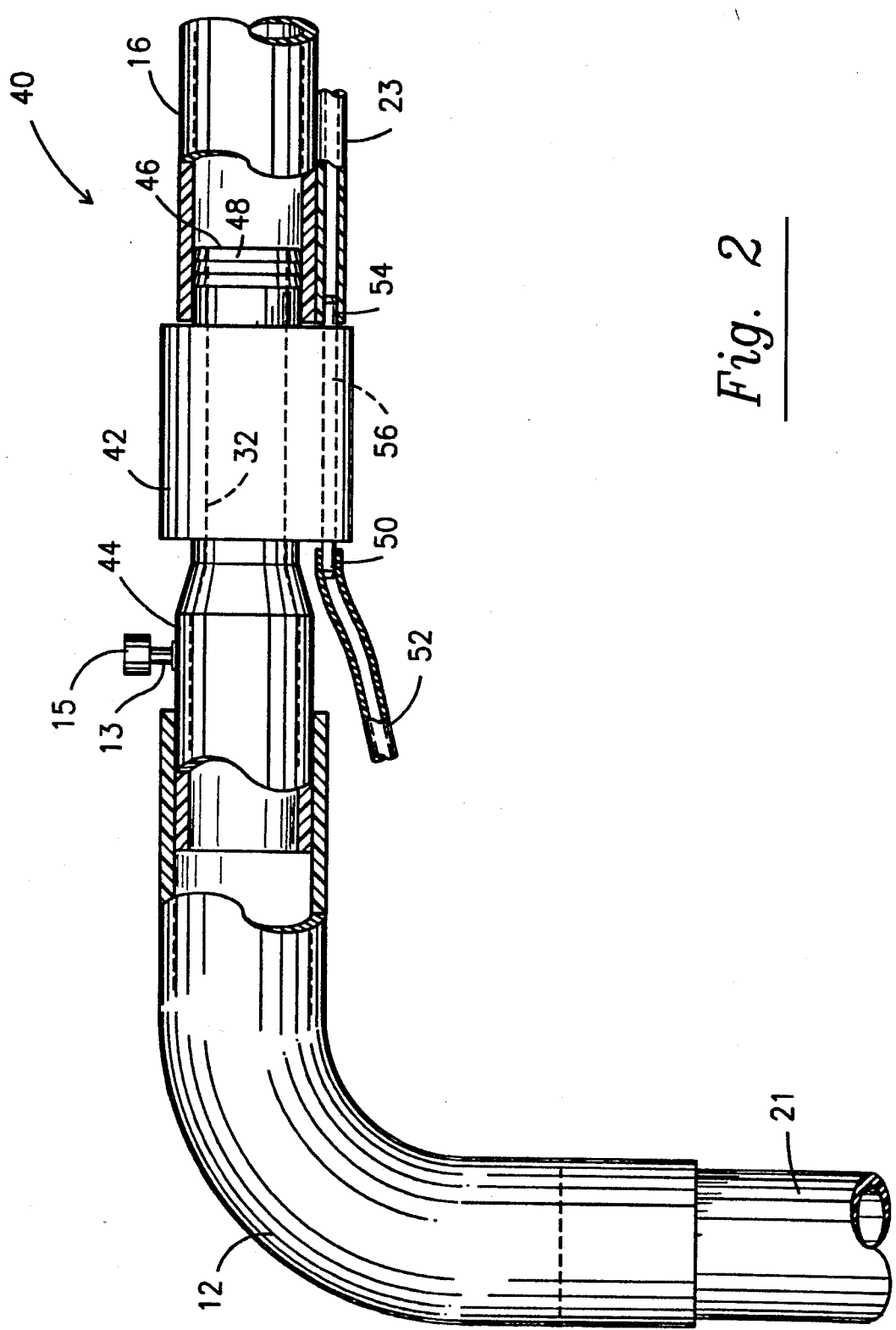
FIG. 2 is a side sectional view of the novel connector.

The improved assembly is shown in FIG. 2 and is denoted 40 as a whole. Significantly, sleeve 14 is eliminated, thereby substantially truncating the assembly. More particularly, the prior art assembly of FIG. 1, exclusive of connector 16, is about eight centimeters in length, whereas the corresponding parts of the FIG. 2 embodiment are about three to five centimeters in length. The novel assembly includes connector 42 having generally tubular mounting member 44 extending from the proximal end thereof and its associated tubular mounting member 46 extending from the distal end thereof. Bore 32, formed in the base of the novel connector 42, provides fluid communication between mounting members 44 and 46. In the claims that follow, mounting members 44 and 46 are referred to as the first and third tubular projections, respectively. The distal end of elbow 12 slidingly press-fittingly engages mounting member 44 without the intervention of sleeve 14, and the proximal end of main endotracheal tube 16 slidingly press-fittingly engages mounting member 46 as shown. Plural annular ridges 48 increase the frictional engagement between tube 16 and mount 46.

An auxiliary mounting member 50 is provided on the proximal end of connector 42, and the distal end of auxiliary tube 52 is slidingly and press-fittingly engaged thereto. In a preferred embodiment of this invention, the diameter of auxiliary tube 52 is at least one millimeter. Another auxiliary mounting member 54 is provided on the distal side of connector 42, and the proximal end of auxiliary lumen 23 is similarly secured thereto. Bore 56, formed in base 42 in parallel relation to bore 32, provides fluid communication between mounting members 50 and 54. In the claims that follow, these auxiliary mounting members are referred to as the second and fourth tubular projections, respectively. Bore 56 provides open communication between lumen 23 and the auxiliary equipment, not shown, at the proximal end of auxiliary tube 52. Note that the bend shown in FIG. 1 has been eliminated, and that the second connector shown in FIG. 1, connector 26, is also eliminated, thereby achieving the objects of this invention.

Note further that first and second fittings 44, 50 are closely radially spaced with respect to one another, as are the third and fourth fittings 46, 54.

Moreover, $CO_2$ port 13 is now formed in tubular mounting member 44; this enables its elimination from elbow 12.

Novel connector 40 is preferably made in a single, integrally formed piece, but it may be manufactured in two or more pieces. It is preferably made of the same materials as the connectors heretofore known.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A connector, comprising:
    a base member of predetermined longitudinal extend having a proximal end and a distal end;
    a first tubular projection disposed on said proximal end of said base member;
    a second tubular projection disposed on said proximal end of said base member;
    a third tubular projection disposed on said distal end of said base member;
    a fourth tubular projection disposed on said distal end of said base member;
    said first, second, third, and fourth tubular projections being disposed in parallel relation to one another;
    a first bore means formed in said base member for providing fluid communication between said first and third tubular projections;
    a second bore means formed in said base member for providing fluid communication between said second and fourth tubular projections;

said first and second bore means being disposed in parallel relation to one another and in parallel relation to said first, second, third, and fourth tubular projections;

a distal end of an anesthesia supply tube being releasably connected to said first tubular projection and a proximal end of an endotracheal tube being releasably connected to said third tubular projection so that anesthesia is delivered to the lungs of a patient;

a distal end of an auxiliary tube being releasably connected to said second tubular projection and a proximal end of an auxiliary lumen being releasably connected to said fourth tubular projection so that conditions in the lungs of said patient are monitored by auxiliary equipment; and whereby a single connector interconnects four tubes and said four tubes are substantially free of bends and constrictions.

2. The connector of claim 1, wherein said endotracheal tube and said auxiliary lumen are integrally formed with one another and share a common length.

3. The connector of claim 1, further comprising a $CO_2$ port formed in said first tubular projection.

4. The connector of claim 3, wherein said $CO_2$ port has a diameter that is at least one millimeter.

5. The connector of claim 1, wherein said auxiliary lumen has a diameter that is at least one millimeter.

* * * * *